United States Patent [19]

Stolka et al.

[11] 4,117,239

[45] Sep. 26, 1978

[54] PROCESS FOR PREPARATION OF 2-ANTHRYL AND SUBSTITUTED 2-ANTHRYL FUNCTIONAL MONOMERS AND POLYMERS

[75] Inventors: Milan Stolka, Fairport; James M. Pearson, Webster; John F. Yanus, Fairport, all of N.Y.

[73] Assignee: Xerox Corporation, Stamford, Conn.

[21] Appl. No.: 556,257

[22] Filed: Mar. 7, 1975

Related U.S. Application Data

[60] Division of Ser. No. 445,705, Feb. 25, 1974, Pat. No. 3,923,762, which is a continuation-in-part of Ser. No. 417,317, Nov. 19, 1973, abandoned.

[51] Int. Cl.$^2$ .............................................. C07C 69/54
[52] U.S. Cl. .................................................. 560/221
[58] Field of Search ........................... 260/486 R, 480; 560/521

[56] References Cited

PUBLICATIONS

J. March, Adv. Org. Chem: Reactions, Mechanisms & Structure, pp. 413–415, 424.
Cram & Hammond: Organic Chem., 2nd ed., pp. 439–440.

*Primary Examiner*—Paul J. Killos
*Attorney, Agent, or Firm*—James J. Ralabate; Albert A. Mahassel; James P. O'Sullivan

[57] ABSTRACT

Process for preparation of 2-anthryl and substituted 2-anthryl functional monomers and polymers. In the process for preparation of these monomers, an anthracenic reactant of the formula:

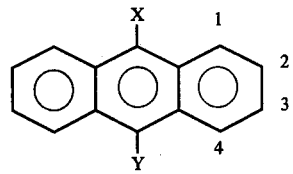

wherein X and Y are independently selected from hydrogen, chlorine, bromine, alkyl of 1 to 4 carbon atoms or phenyl is acylated in nitrobenzene under conditions which favor reaction at the two position. The resulting acylated product can then be (a) reacted with an alkylidenephosphorane (Wittig synthesis) or (b) reduced to the corresponding alcohol. Subsequent to such reduction, this alcohol can undergo further modification at the hydroxyl function to form a polymerizable addition monomer. Through the proper selection of the relative concentration of reactants and control over processing conditions, it is possible not only to prepare such monomers in high yields but also upon polymerization of such monomers, to obtain high molecular weight 2-anthryl and substituted 2-anthryl functional polymers (molecular weight of at least 10$^4$). Polymers of such high molecular weight can readily be formed without the use of binders into self-supporting films. Such films are intrinsically photoconductive in the ultraviolet region of the electromagnetic spectrum and have good transport capabilities for charge carriers of both polarities.

70 Claims, No Drawings

PROCESS FOR PREPARATION OF 2-ANTHRYL AND SUBSTITUTED 2-ANTHRYL FUNCTIONAL MONOMERS AND POLYMERS

CROSS REFERENCE TO RELATED APPLICATIONS

This is a division of application Ser. No. 445,705, filed Feb. 25, 1074, now U.S. Pat. No. 3,923,762, which is a continuationin-part of Ser. No. 417,317 filed Nov. 19, 1973, now abandoned.

BACKGROUND OF THE INVENTION

1. Field of the Invention

This invention relates to processes and products of said processes. More specifically, this invention involves a high yield process for preparation of 2-anthryl and substituted 2-anthryl functional monomers. The monomers resulting from such processes can be polymerized to high molecular weight ($\overline{M}_w \geq 10^4$, degree of polymerization ~40 or greater). These polymers readily form self-supporting films which are intrinsically photoconductive in the ultraviolet region of the electromagnetic spectrum.

2. Description of the Prior Art

The formation and development of images on the imaging layers of photoconductive materials by electrostatic means is well-known. The best known of the commercial processes, more commonly known as xerography, involves forming a latent electrostatic image on the imaging layer of an imaging member by first uniformly electrostatically charging the surface of the imaging layer in the dark and then exposing this electrostatically charged surface to a light and shadow image. The light struck areas of the imaging layer are thus rendered conductive and the electrostatic charge selectively dissipated in thse irradiated areas. After the photoconductor is exposed, the latent electrostatic image on this image bearing surface is rendered visible by development with a finely divided colored electroscopic material, known in the art as "toner". This toner will be principally attracted to those areas on the image bearing surface which retain the electrostatic charge and thus form a visible powder image.

The developed image can then be read or permanently affixed to the photoconductor where the imaging layer is not to be reused. This latter practice is usually followed with respect to the binder type photoconductive films (e.g. zinc oxide pigment in a film forming insulating resin) where the photoconductive imaging layer is also an integral part of the finished copy. In so-called "plain paper" copying systems, the latent image can be developed on the imaging surface of a resuable photoconductor or transferred to another surface, such as a sheet of paper, and thereafter developed. When the latent image is developed on the imaging surface of a reusable photoconductor, it is subsequently transferred to another substrate and subsequently permanently affixed thereto. Anyone of a variety of well-known techniques can be used to permanently affix the toner image to the copy sheet, including overcoating with transparent films, and solvent or thermal fusion of the toner particles to this support of substrate.

In the above "plain paper" copying systems, the materials used in the photoconductive layer should preferably be capable of rapid switching from insulating to conductive to insulating state in order to permit cyclic use of the imaging layer. The increase in the rate of dark decay of the photoconductor. This phenomenon, commonly referred to in the art as "fatigue", has in the past been avoided by the selection of photoconductive materials possessing rapid switching capacity. Typical of the materials suitable for use in such a rapidly cycling imaging system include anthracene, sulfur, selenium and mixtures thereof (U.S. Pat. No. 2,297,691); selenium being preferred because of its superior photosensitivity.

In the past, the use of anthracene in photoconductive insulating layers has been limited exclusively to the inclusion of the crystalline form of this material in a binder, since high molecular weight anthracene functional polymers have been virtually impossible to prepare. For example, attempts to synthesize high molecular weight anthracene polymers from 9-vinylanthracene by free radical initiated polymerization techniques generaly yields only oligomers. Attempts at cationic polymerization of these same monomers yields only low molecular weight materials of questionable structure; postulated to be a mixture of low molecular weight polymeric materials containing structural units from 9-vinylanthracene and 9,10-dimethyleneanthracene. Anionic polymerization of 9-vinylanthracene also yields only oligomers having a degree of polymerization in the range of from about 4 – 12. Attempts to copolymerize 9-vinylanthracene with other monomers, such as styrene, does not apparently improve the chances of obtaining polymeric products of high molecular weight. Apparently, resonance stabilization of the anthracene free radical under the conditions prevailing during such polymerization, favors formation of a non-propagating radical thus preventing the further growth of the polymer chain, A. Rembaum et al, Macromol Rev. 1, 57 (1967).

Apparent attempts at preparation of homopolymers of 2-vinylanthracene and 1-vinylanthracene and styrene copolymers thereof have proven equally fruitless, yielding only low molecular weight products.

Recently, the synthesis of copolymers of 9-anthrylethyl acrylate and methyl methacrylate has met with limited success; Vysokomolekulyarnye Soedineniya A14(5): 1127-31 (1972). The anthracene functionality of these copolymers (generally less than 11 %) provides luminescent markers (scintilators) for assistance in the study of the relaxation properties and conformation transformation of methyl methacrylate. Other copolymers containing anthracene groups have also been synthesized including polycondensates, formaldehyde resins, oligoarylenes; however, all of these polymeric products have relatively poor mechanical properties and cannot be readily formed into self-supporting films.

It is, therefore, the object of this invention to remove the above as well as related deficiencies in the prior art systems.

More specifically, it is the principle object of this invention to provide a process for preparation of anthracenic monomers in high yields.

Another object of this invention is to provide anthracenic monomers which can be readily polymerized into high moelcular weight anthracenic functional polymers.

Still another object of this invention is to provide a process for polymerization of such anthracenic monomers into anthracenic functional polymers.

Yet another object of this invention is to provide a high molecular weight scintilating polymer having anthracenic functionality.

It is a further object of this invention to provide an anthracenic functional polymer suitable for use in photoconductive imaging members and methods.

SUMMARY OF THE INVENTION

The above and related objects are achieved by providing a process for preparation of 2-anthryl and substituted 2-anthryl functional monomers of the formulae

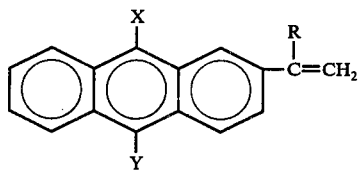

wherein

R is hydrogen or alkyl of 1 to about 3 carbon atoms; and X and Y are independently selcted from hydrogen, chlorine, bromine, alkyl of 1 - 4 carbon atoms, or phenyl. -and-

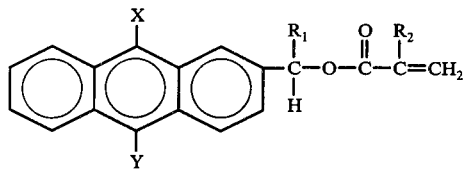

wherein $R_1$ is hydrogen or alkyl of 1 - 6 carbon atoms; $R_2$ is alkyl of 1 - 4 carbon atoms; and X and Y are independently selected hydrogen from chlorine, bromine, alkyl of 1 - 4 carbon atoms, or phenyl In these processes, a nitrobenzene dispersion containing an anthracene reactant of the formula

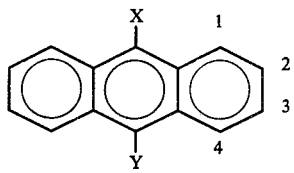

wherein X and Y are independently selected from hydrogen, chlorine, bromine, alkyl of 1 -4 carbon atoms or phenyl
is contacted with a separate solution containing a complex of an acylating agent and a Lewis Acid at a temperature of from about 5 to about 50° C for an interval sufficient to effect acylation of at least some of the anthracenic reactant at the 2-position. The relative molar ratio of acylating agent to Leis Acid in said separate solution is preferably 1:3 (in the case of the acylating agent being an acid anhydride) or 1:1 (in the case of the acylating agent being an acid or acid chloride); and the relative molar ratio of acylating agent to anthracenic reactant is preferably 2:1 or slightly greater. The acylated anthracenic reactant is then further modified at the carbonyl site whereby a 2-anthryl or 2 substituted 2-anthryl functional addition monomer is prepared. The procedures and reactants used in such modification will vary with the specific addition monomer desired.

DESCRIPTION OF THE INVENTION INCLUDING PREFERRED EMBODIMENTS

Preliminary to preparation of such monomers, two separate mixtures are prepared; one containing the anthracenic reactant and a second containing a complex of Lewis Acid and acylating agent. The relative molar ratio of Lewis Acid to acylating agent in such mixtures can range from about 0.5:1 to about 5:1, with best results being obtained where slightly in excess of an equimolar amount of Lewis Acid is present. It is essential to maintain a constant ratio of Lewis Acid to acylating agent in the presence of the anthracenic reactant for reproducibly high yields of acylated product. Typical of the Lewis Acids which can be used in such second solution include aluminum chloride, aluminum bromide, phosphorous chloride, ferric chloride, stannic chloride, titanium tetrachloride, boron chloride, zirconium tetra chloride, and sodium aluminum chloride. Representative of the acylating agents which can be suitably complexed with the above Lewis Acids include acetic acid, acetic anhydride and acetyl chloride.

The relative molar ratio of acylating agent to the anthracenic reactant must also be carefully adjusted in order to insure that the reaction equilibrium favors the acylation of the anthracenic reactant at the 2-position. Good results have been attained where the molar ratio of acylating aent to anthracenic reactant is in the range of from about 1:1 to about 5:1 and preferably about 2:1. It is also advisable to limit the volume of nitrobenzene in the reaction medium to the minimum amount required for dissolving the anthracenic reactant and the Lewis Acid/acylating agent. The presence of excessive amounts of nitrobenzene can result in some loss of acylated product due to problems of isolation of this product from the solvent. It is generally preferred that the volume of nitrobenzene be limited from about 600 to about 1500 milliliters solvent per 150 grams of anthracenic reactant; this amount inclusive of the amount of nitrobenzene necessary to prepare both the solution containing the anthracenic reactant and the solution containing the Lewis Acid/acylating agent complex.

In addition to nitrobenzene by itself, solvent mixtures containing predominantly nitrobenzene (in excess of 50% by volume) and other organic liquids can also be used as the vehicle in which the acylation of the anthracenic reactant takes place. However, as other solvents are introduced into the reaction medium, the directivity of acylation at the 2-position rapidly progressively decreases. Representative of the solvents which can be used in combination with nitrobenzene as the vehicle for carrying out the acylation of the anthracenic reactant include carbon tetrachloride, carbon disulfide and chloroform; and, however, yields of desired product will show an appreciable decline. Subsequent to preparation of separate solutions containing the anthracenic reactant and the Lewis Acid/acylating agent complex, the two solutions are combined by the gradual addition of the solution containing the Lewis Acid/acylating agent complex to the anthracenic reactant solution over a period of from about 15 minutes to about 60 minutes. Upon completion of combination of the two solutions, the ingredients contained therein are allowed to react for an additional period of from about 1 to 20 hours. The temperature of this combined solution is maintained within a range of from about 5° to about 50° C and preferably within a range of from about 10° to about 30° C during the mixing and the reaction of the ingredients of the two solutions.

It is also advisable, although not critical, to carry out this acylation reaction in an inert non-oxidizing atmosphere. Moreover, because of the photoactive nature of such anthracenic materials, the reaction mass should also be shielded from activating electromagnetic radiation. The acylation reaction is terminated by precipitation of an acylated anthracenic reactant/Lewis Acid complex from the nitrobenzene solution by the addition of a non-solvent of this complex to the reaction mixture. Solvents which are suitable for precipitation of such materials includes benzene, toluene and carbon tetrachloride. The volume of solvent used in precipitation of this complex must be carefully controlled so as to avoid "oiling out" of the desired product and thus making its recovery more difficult. The precipitated complex is then decomposed with aqueous hydrochloric acid and the product thereafter dried. The acylated product thus obtained, (hereinafter referred to as the "intermediate") is further purified by recrystallization from ethanol, benzene or other suitable solvents.

The intermediate prepared as described above can now be further modified at the carbonyl oxygen by any one of a variety of reactions depending upon the specific monomer desired. For example, $\alpha$-alkyl vinyl monomers corresponding to formula I can be prepared by simply reacting the carbonyl functional anthracenic reactant with an alkylideneposphorane in accord with the procedures described by Wittig et al, Ber. 87, 1318 (1954) and Ber. 88, 1654 (1955). Alternatively, the above intermediate can be reduced to the corresponding alcohol by a process involving first dispersion the intermediate in an appropriate organic solvent, such as lower alkyl alcohols, tetrahydrofuran, ethers or diglyme. To this dispersion is subsequently added a reducing agent such as sodium borohydride, potassium borohydride, lithium aluminum hydride/aluminum chloride, and lithium aluminium hydride/boronfluoride; the boronhydride reducing agents being generally preferred. The relative molar concentration intermediate to reducing agent should be at least 1:1 and preferably in excess of equimolar amounts of reducing agent should be used. Upon completion of addition of the reducing agent to the intermediate solution, the resulting mixture is heated to boiling under reflux conditions for about 4 hours and then the reflux condenser opened to permit removal of volatile solvent contained therein residues. The solid residues remaining in the reaction vessel upon evaporation of such solvents are then allowed to cool to room temperature and thereafter contacted with aqueous hydrochloric acid for decomposition of residual traces of reducing agent which may be present in the isolated product. The solid reaction product thus obtained can be separated from this acidic solution by filtration or extracted with ether and the solids isolated from the extractant by conventional means.

Monomers corresponding to formula I can be prepared from this anthracenic alcohol by at least two convenient routes. For example, the alcohol can be initially reacted with a metal halide or acid halide (e.g. thionyl chloride) whereby the hydroxyl group of the alcohol is displaced by a halogen atom. Following such displacement, the resulting halogenated anthracene functional compound is heated in a basic solution (e.g. $Li_2CO_3$ in dimethylformamide) for an interval sufficient to cause its dehydrohalogenation and thus formation of the vinyl analogue. A second route which can be used in conversion of the alcohol to the vinyl monomer involves simply heating of said alcohol over a paladium catalyst for an interval sufficient to cause its dehydration.

Monomers corresponding to formula II can be prepared from the above anthracenic alcohol by condensation of an alpha alkyl acryloyl halide with said alcohol in a suitable solvent, such as dioxane. It is also suggested that a small quantity of triethylamine be present in said solution in order to absorb the acid generated as a result of the condensation of these materials and thus avoid subsequent hydrolysis of the desired reaction product once it has formed. In the event that one or more of the above materials is not readily soluble in the reaction medium, this medium can be gradually heated until all reactants are completely dissolved. It is also recommended that the relative concentration of alpha alkyl acryloyl halide to anthracenic alcohol be adequate to achieve substantially complete condensation of the two materials. Good results are obtained where equimolar amounts of the two reactants are present in the solution and preferably where there is a slight molar excess of alpha alkyl acryloyl halide. Following completion of the addition of said reactants to the reaction medium the monomer will begin to form, as evidenced by the appearance of the precipitate at the bottom of the reaction vessel. The reaction can be allowed to proceed for up to about 24 hours whereupon it is terminated by the addition of water to the reaction medium. The addition of water causes increased precipitation of monomer. Unreacted alpha acryloyl halide dissolves in the water and is thus readily separated from the monomeric product. Monomer solids can then be recovered from the reaction medium by filtration, dried and recrystallized from a benzene/hexane solvent mixture.

It is both essential and critical that the monomers prepared as described above are isolated in a manner which minimizes oxidation of the anthracene and substituted anthracene functional groups. This can be achieved by carrying out the precipitation, separation and recrystallization of these monomers under a blanket of inert nonoxidizing gas, such as argon or nitrogen. Upon obtaining the desired monomeric materials, they are stored either in a vacuum or in an inert nonoxidizing atmosphere. Prior to polymerization of such monomers they are further purified for the removal of oxidation products. In order to further insure that the monomer is devoid of oxidation products of the anthracene and substituted anthracene functional groups, a solution of the monomer is passed through a column of activated neutral or basic alumina, the pure monomer collected, and the eluent evaporated therefrom under a vacuum. Such purification procedures must also be carried out in a nonoxidizing atmosphere.

The vinyl monomers (formula I) prepared as described above can be polymerized in a non-oxidizing atmosphere by a free radical, anionic or cationic polymerization mechanism. Initiator compounds which are suitable for use in such free radical initiated addition polymerizations include the various peroxides or azo-bisisobutyronitrile and analogous initiators. Anionic polymerization of these monomers also yields highly satisfactory polymers. It is generally preferred that such anionic polymerization system be maintained below about 0° C, (in order to avoid the type of inhibiting processes which commonly occur at higher temperatures), and that such polymerization be initiated with an "addition" type initiator. Cationic polymerization is the least preferred of the three systems due to the relatively low molecular weights of the polymers produced thereby.

Acrylate monomers corresponding to formula II can be formed into polymers by standard free radical initiated addition polymerization techniques. Of course, until substantially all of the monomer has been polymerized the environment within the reaction vessel should remain substantially free of oxygen. Many of the peroxide initiators traditionally used in free radial polymerization systems have been known to affect hydrogen abstraction of such acrylate polymers, resulting in cross-linking of these materials. Therefore, it is generally preferred that free radical initiated addition polymerization of these monomer be carried out with azobisisobutyronitrile and analogous initiator materials.

Once having prepared such polymer resins, they are separated from their respective polymerization media and dried. These resins can then be readily dissolved in a number of organic solvents, such as tetrahydrofuran, dimethylformamide, toluene, cyclohexanone or their respective solvent mixtures, and the resulting solutions sprayed, draw, dipped and/or melt coated on a suitable (preferably conductive) substrate. The ease with which such polymers can be dissolved in the above organic solvents in one of the unique characteristics of the polymers prepared by the process of this invention. The amount of such polymers which is imparted to the substrate can vary with the contemplated utility of the film. After applying a coating of these materials to the substrate, the resultant film is allowed to dry until substantially free of residual solvent. In the event that the polymer solution is spray coated onto such a substrate, the resulting dry film may possess a rough surface texture. Such surface roughness can be eliminated by simply heating this polymer coating sufficiently to cause it to flow.

The quantity of polymer applied to such substrates is carefully monitored in order to insure that the resulting coating is both coherent and forms a substantially uniform film on the supportive member. Generally, film thickness is controlled in a dip coating application by the adjustment of the viscosity of the coating solution and/or by control of the temperature and humidity of the post coating environment. In the event that the polymeric layer is prepared by solvent casting of a polymer solution on a supportive member, mechanical means can also be used in addition to adjustment of viscosity in control the film thickness of the polymer coating. For example, the use of a doctor blade having a wet gap setting of about 0.005 inches to assist in spreading of the resinous dispersion on a substrate will insure that the resultant film thickness of said coating will not exceed about 15 microns. Films prepared from such polymeric materials having a thickness in the range of from about 0.1 to about 300 microns can be used in conventional electrophotographic imaging members either as the charge carrier generating element or as an electronically active matrix for the transport of charge carriers generated by another photoconductive material; separation of carrier generation and transport being disclosed in UK Pat. Nos. 1,337,228 and 1,343,671 which are hereby incorporated by referenced in their entirety.

Virtually, any of the traditionally employed conductive self-supporting substrates used in the preparation of electrophotographic imaging members can be operatively associated with such films. Typical of the conductive materials which can be satisfactorily used as the substrates of such imaging members include aluminum; chromium; stainless steel, brass; copper; beryllium copper; their respective alloys; metalized plastic films, metal coated plastic films (e.g. polyethylene terephthalate coated with vacuum deposit aluminum); and glass substrates having conductive oxide having coatings.

The film prepared from these polymer compositions, as indicated previously are photoconductive in the ultraviolet region of the electromagnetic spectrum. In order to shift the photoresponsiveness of such materials into the visible region of the spectrum such polymers can be sensitized by the addition of a dyestuff or an activator (e.g. an electron donor and/or electron acceptor material). The concentration of such sensitizers within the polymer must be sufficient to extend the absorption of said materials into the visible range. Generally, anywhere from about 0.1 to about 10 weight percent of such sensitizers is sufficient to achieve such enhancement in spectral response.

It may also be desirable in order to enhance or modify the physical and/or electrical properties of the polymers of this invention to copolymerize one or more of the above monomers with a non-anthracenic monomer. The resulting copolymer will of course vary with the relative reactivity ratio of the monomers present in the charge and the manner in which such polymerization is carried out. For example, many of the above anthracenic polymer segments may be copolymerized with elastomers in order to enhance the flexibility of a film of such materials.

The Examples which follow further define, describe and illustrate the various processes of this invention and the products produced thereby. Apparatus and techniques used in such processes and evaluation of their respective products are standard or as hereinbefore described. Parts and percentages appearing in such Examples are by weight unless otherwise indicated.

EXAMPLE I

Into a 5 liter flask containing 150 milliliters nitrobenzene is dispersed about 150 grams (0.84 moles) of anthracene. The flask and its contents are purged of air with nitrogen and thereafter cooled to about 15° C. In a separate flask containing 500 milliliters nitrobenzene is dispersed 255 grams (1.9 moles) of anhydrous aluminum chloride. To this aluminum chloride solution is slowly added 150 milliliters (1.6 moles) of acetic anhydride. The aluminum chloride solution is vigorously agitated during such addition. The aluminum chloride/acetic anhydride complex prepared as described above is now combined with the anthracene dispersion by gradual dropwise addition of this complex to the anthracene over a period of approximately one hour. The temperature of the resulting mixture is maintained at about 15° C subsequent to completion of said addition. AFter 18 hours, the reaction of these materials is quenched by the addition of about 1800 milliliters of dry benzene to the combined solution. The reaction mixture is stirred for an additional 4 hours, the precipitated complex contained therein separated from the liquid by filtration, washed with approximately 200 milliliters benzene and then washed again with an greater amounts of hexane. The solid complex is now hydrolyzed in a dilute acid solution (2% hydrochloric acid), the resulting product separated from the hydrolyzed medium by filtration, washed to neutral raction with water, dried and recrystallized from a benzene/hexane solution after charcoal treatment. The product thus obtained, 2-anthrylmethyl ketone, is a yellow-green powder, M.P. 188° C. Yield: 98 grams.

EXAMPLE II

In order to demonstrate the criticality of formation of the complex between the Lewis Acid and the acylating agent prior to admixture with anthracene, the procedures of Example I are repeated except for the separate addition of acetic anhydride and aluminum chloride to the anthracene dispersion.

About 150 grams of anthracene is dispersed in a reaction vessel containing 200 milliliters nitrobenzene and 150 milliliters acetic anhydride. The mixture is cooled to about 15° C and both the vessel and its contents purged of air with nitrogen. In a separate flask, 255 grams of anhydrous aluminum chloride is dissolved in 500 milliliters of nitrobenzene. This aluminum chloride solution is added by dropwise addition to the vessel containing the anthracene/acetic anhydride mixture. During such addition the contents of the reaction vessel are maintained in a constant state of agitation. Upon completion of addition of the aluminum chloride solution to the reaction vessel, the contents of said vessel are stirred for an additional 18 hours at 15° C. The complex formed by the reaction of the materials within the reaction vessel is precipitated from solution by the addition thereto of 1800 milliliters of dry benzene. After 4 hours, the precipitation of the complex is complete and it is separated from the reaction medium by filtration, dried and recrystallized from a benzene/hexane solution after charcoal treatment. M.P. 187° – 188° C. Yield: 8 grams.

It is evident that the separate addition of the Lewis Acid and the acylating agent to the anthracenic reactant dramatically reduces the yield of the intended product.

EXAMPLE III

The procedures of Example II are repeated with identical amounts of reactants under identical conditions. The product obtained has a melting point of 187° – 188° C. Yield: 35 grams.

EXAMPLE IV

Example II is repeated with identical amounts of reactants under identical conditions. The melting point of the product thus obtained is 187° – 188° C. Yield: less than 1 gram.

Comparision of the results of Example II, III and IV indicate that where the Lewis Acid and acylating agent are separately added to the anthracenic reactant, reproducibility of the reaction, especially with regard to yield of desired product, is purely a matter of chance.

EXAMPLE V

The procedure of Example II is substantially repeated except for the substitution of benzene for nitrobenzene as the reaction vehicle.

About 89 grams (0.5 moles) of anthracene is dispersed in a reaction vessel containing 500 milliliters benzene and 113 milliliters (1.5 moles) of acetyl chloride. 200 grams of anhydrous aluminum chloride is added to the reaction vessel in small increments over a period of 1 hour. The resulting mixture is stirred in an ice bath for about 90 minutes and the temperature thereafter allowed to rise to about 25° C. The contents of the reaction vessel is stirred for an additional 18 hours, the reaction of materials contained therein quenched by the addition of ice water, the reaction product extracted with benzene, washed with water and dried. Benzene remaining in the product evaporated during drying however, acetophenone residues remaining in the product are removed in vacuo. The product thus obtained is recrystallized (x2) from heptane/benzene mixtures (10:1) with charcoal treatment and then again from ethanol (x2). Yield 5 grams of 2 - anthryl methyl ketone, M.P. 185° – 186° C.

It is evident that the substitution of benzene for nitrobenzene of Example II also results in yields substantially less than that obtainable by Example I and further introduces impurities within the desired product requiring separate removal.

EXAMPLE VI

The procedure of Example I is repeated except for a shift in the relative concentration of aluminum chloride from 255 grams to about 127 grams. Yield: 27.5 grams of 2-anthryl methyl ketone, M.P. 187° C.

It is evident from this Example that the relative concentration of aluminum chloride is critical in yield of the desired product since a 50% reduction in aluminum chloride results in approximately a 75% reduction in the desired product.

EXAMPLE VII

The procedures of Example I are repeated except for a shift in the relative concentration of acetic anhydride used in the acylating complex from 155 milliliters to 80 milliliters. Yield: 45 grams of 2-anthryl methyl ketone, M.P. 187° – 188° C.

It is evident from this Example that the yield of product is approximately directly proportional to the concentration of acetic anhydride used in formation of the acylating agent complex.

EXAMPLE VIII

About 53 grams of the product of Example I is added to a 3 liter flask containing 1800 milliliters ethanol, the reaction vessel and its contents purged of air with nitrogen, heated to boiling under reflux conditions and 25 grams of sodium borohydride in 280 milliliters of water slowly added thereto. The mixture becomes increasingly homogenous when about ⅔ of the total borohydride solution has been added. The solution is heated to boiling under reflux for about 2 hours, its volume reduced by about ⅓ by evaporation of some of the ethanol and the product contained therein isolated by precipitation with a slightly acidic aqueous solution. The precipitated product is separated from the reaction vehicle by filtration, washed with water, dried and recrystallized from benzene with charcoal treatment. Yield: 50 grams of alpha-(2-anthryl) ethanol, M.P. 164° C.

About 50 grams of alpha-(2-anthryl) ethanol is dissolved in 600 milliliters of anhydrous benzene and heated to boiling under reflux conditions. To this boiling solution is then added 20 milliliters of thionyl chloride. The addition of the thionyl chloride to the alcohol solution proceeds very gradually in the beginning and then more rapidly as the reaction between these materials begins to take place. Subsequent to the addition of the thionyl chloride, the reaction vessel is purged with nitrogen and the contents of the flask heated under this nitrogen blanket for an additional three hours, allowed to cool to room temperature and poured into about 1.2 liters of petroleum ether. The product thus obtained is separated from the ether by filtration, washed with additional amounts of petroleum ether and recrystallized from a benzene/hexane solution. Yield: 46 grams of light green powder, alpha-(2-anthryl) chloroethane, M.P. 170 to 178 (with decomposition).

About 45 grams of alpha-(2-anthryl) chloroethane is added to 350 milliliters of dimethylformamide containing 25 grams of lithium carbonate. The reaction vessel containing this mixture is purged of air with nitrogen, heated to 130° C and maintained at this temperature for a period of about 4 hours. The contents of the reaction vessel are then poured into a very dilute solution of aqueous hydrochloric acid. The product thus obtained is separated from the acidic medium by filtration, dried, recrystallized three times from benzene/hexane solutions after treatment with charcoal. Yield: 30 grams of a yellow powder, 2-vinylanthracene, M.P. 210° C.

Subsequent to its preparation the 2-vinylanthracene is recrystallized at least one more time from benzene/hexane solution, dissolved in a degassed benzene/hexane mixture and passed through a column of basic alumina which has been shielded from light. The monomer is eluted with degassed benzene, the eluent being collected in a light tight ampule under an argon blanket. The shielded ampule containing the purified monomer is then attached to a vacuum line, the solvent evaporated therefrom and the ampule sealed. The monomer can be stored without any adverse effects provided it is shielded from light (especially ultraviolet light).

The monomer in the ampule (approximately 1 gram) can be polymerized by standard free radical initiated addition polymerization techniques by simply injecting a solution comprising 8 milliliters of xylene (which has been previously purified by passage through a column of activated alumina and subsequently degassed) and 0.05 milliliters of di-t-butyl peroxide through a side-arm of the ampule. Argon gas is used to assist the infusion of the xylene initiator solution into the ampule. Following infusion of the above materials into the ampule, the ampule is inserted into liquid nitrogen whereupon the solution contained therein freezes and the residual gasses within the ampule removed by a vacuum. Subsequent to removal of gas from the ampule, it is resealed and heated for 48 hours at 115° C. The ampule is then opened and the polymer precipitated with methanol, recovered by the filtration, dried and reprecipitated from a benzene solution with methanol. Yield: 0.97 grams of poly(2-vinylanthracene), $\overline{M}_w = 80,000$ as determined by gel permeation chromotography and light scattering techniques.

EXAMPLE IX

The following Example illustrates the cationic polymerization of a monomer prepared as described in Example VIII. Preliminary to such polymerization, 20 milliliters of methylene chloride (having been previously purified by passage through a column of activated alumina and degassed) is vacuum distilled into a sealed light tight ampule containing about 2 grams of 2-vinylanthracene. After the monomer is dissolved, about 1 milliliter of catalyst solution (0.2 milliliters boron trifluoride etherate in 200 milliliters of similarly purified methylene chloride) is also introduced into the ampule, the ampule resealed and the combined solution heated to about 35° C. After about 48 hours of continuous heating or stirring, the polymerization is quenched and polymer solids precipitated by pouring the contents of the ampule into methanol. The precipitated polymer solids are separated from the methanol by filtration and reprecipitated from benzene with methanol. Yield: 0.6 grams of yellow powder, $\overline{M}_w = 18,000$ (as determined by gel permeation chromotography).

EXAMPLE X

The procedures of Example IX are repeated except for the preexposure of the monomer to air and diffuse roomlight for about one hour prior to attempting its polymerization. The monomer could not be thereafter polymerized.

EXAMPLE XI

The following Example illustrates the anionic polymerization of a monomer prepared as described in Example VIII. Preliminary to such polymerization, 200 milliliters of dried, oxygen free tetrahydrofuran is vacuum distilled into a light tight ampule containing 3 grams of 2-vinylanthracene. After the monomer is dissolved, the ampule and its contents are chilled to −78° C, and about 5 milliliters of initiator solution (5 × 10⁻⁵ moles of the sodium salt of alpha methyl styrene tetramer in tetrahydrofuran) injected into the ampule through a side arm on the ampule. Polymerization of the monomer proceeds upon the combination of these two solutions. After five days of continuous stirring at −78° C, the contents of the ampule are poured into methanol for precipitation of the polymer. The polymer solids are then recovered from the methanol by filtration and reprecipitated from benzene with methanol for removal of impurities, monomer residues and low molecular weight fractions. Yield: 3.0 grams of white polymer $\overline{M}_w = 1,000,000$, $\overline{M}_w/Mn$ 2.87.

EXAMPLE XII

The anionic polymerization of 2-vinylanthracene is repeated according to the procedures of Example XI with the following modifications: the polymerization temperature is increased from −78° C to −32° C and reaction time extended from 5 days to 20 days. Yield: 3.0 grams of white polymer $\overline{M}_w = 2,890,000$ $\overline{M}_w/Mn$ 10.1.

EXAMPLE XIII

The anionic polymerization of 2-vinylanthracene is repeated according to the procedures of Example XI with the following modifications: prior to initiation of polymerization, the monomer is exposed to air and diffuse roomlight for one hour. The monomer cannot thereafter be polymerized.

EXAMPLE XIV

Preparation of 2-(2-anthryl) propene

Into a 500 milliliter flask which has been purged of air with nitrogen are placed 16.6 grams of triphenylmethylphosphoniumbromide and 100 milliliters of tetrahydrofuran. After the contents of the flask are in solution, the flask is chilled to 0° C, and 21 milliliter of butyl lithium solution (2.2 moles/liter of hexane) also introduced into the flask. The combined solution is stirred at 0° C for 16 hours under nitrogen and then the temperature of the solution allowed to increase to room temperature (approximately 20° C). About 2 grams of 2-anthryl methyl ketone (prepared according to the procedures described in Example I) in 250 milliliters of tetrahydrofuran are now added to the above solution, the combined solution heated to boiling under reflux conditions, and the volume of the contents of the flask reduced by about 250 milliliters over a period of 90 minutes through the controlled evaporation of tetrahydrofuran. The darkly colored solution remaining in the flask is cooled to room temperature, poured into an alcoholic solution (50:50 ethanol and water) for precipitation of the monomer the monomer solids separated from the alcoholic solution by filtration, dried and reprecipitated from hexane/heptane mixtures. Yield: 8.8 grams of crude monomer. The monomer is further purified according to the procedures described in Example VIII. The resulting monomer, 2-(2-anthryl) propene, is a white powder, MP = 153° C.

About 100 milliliters of tetrahydrofuran is vacuum distilled into a light tight ampule containing the above monomer, the ampule chilled to the temperature of dry ice (approximately −40° C) and about 5 milliliters of initiator solution (5 × $10^{-5}$ moles of the sodium salt of alphamethyl styrene tetramer in tetrahydrofuran) injected into the ampule through a side arm on the ampule. Polymerization of the monomer commences upon the introduction of the initiator into the ampule. After about 24 hours of continuous stirring at −40° C, the contents of the ampule are emptied into a flask containing methanol thereby quenching the polymerization reaction and precipitating the polymer. The polymer solids are recovered from the methanol solution by filtration, dried and reprecipitated from benzene with methanol. Yield: 8.0 grams of white polymer, $\overline{M}_w$ 280,000, $\overline{M}_w/Mn$ 1.74.

EXAMPLE XV

Preparation of poly(1(2-anthryl)-ethyl methacrylate)

About 0.84 moles (150 grams) of anthracene is dispersed in 150 milliliters nitrobenzene. This dispersion is prepared in a reaction vessel equipped with an addition funnel, a thermometer, a source of non-oxidizing gas and a magnetic stirring bar. The dispersion is chilled to about 15° C. In a separate container about 1.9 moles (255 grams) of aluminum chloride is dissolved in 480 milliliters nitrobenzene. About 1.6 moles (155 milliliters) acetic anhydride is added to the aluminum chloride solution by dropwise addition. The aluminum chloride solution is rapidly agitated during such addition. The temperature of this solution is carefully monitored since the formation of the complex between the aluminum chloride and the acetic anhydride is strongly exothermic. Subsequent to formation of this complex, it is transferred to the addition funnel. The reaction vessel containing the anthracene dispersion is vigorously agitated and the aluminum chloride/acetic anhydride complex added dropwise over a period of about 60 minutes. The temperature of the anthracene dispersion is maintained at 15° during the addition of this complex. About 5 hours after completion of addition of the complex to the anthracene dispersion, the reaction of these materials is quenched by the addition of 1500 milliliters of cold, dry benzene (cooled to ~8° C). The reaction vessel is chilled in an ice bath after the addition of benzene and maintained at this temperature for approximately 4 hours. The red solids formed during this reaction are separated from the reaction mass by filtration, washed with additional amounts of dry benzene and hexane for removal of nitrobenzene residues from the solids. The filtration and subsequent washing of the recovered solids should be performed in a low humidity environment in order to prevent premature hydrolysis of the recovered solid product. Subsequent to removal of residual traces of nitrobenzene from this product, it is hydrolyzed in an aqueous solution of hydrochloric acid (200 milliliters of concentrated HCl per 2 liters distilled water). The solids are then recovered by filtration, washed continuously with distilled water until all traces of acidity are removed, dried in a vacuum oven and purified by recrystallization from a benzene/hexane (1:1) solvent mixture. The recovered product, 2-acetyl-anthracene, is light-green in appearance. Yield: 98 grams, MP 188° C.

About 53 grams of 2-acetyl anthracene is dispersed in 1800 milliliters of ethanol, the dispersion heated to boiling under reflux conditions and 25 grams of sodium borohydride in 280 milliliters distilled water added by dropwise addition. During the addition of the sodium borohydride, the dispersion is maintained in a constant state of mild agitation. With the addition of about two-thirds of the sodium borohydride solution, the dispersed matter dissolves in the solvent and turns brown in color. Upon completion of addition of the sodium borohydride, the resulting solution is heated under reflux conditions for an additional two hours. At this time, the reflux condensor is opened and approximately ⅔ of the volatile solvents contained within the mixture allowed to escape. The product remaining in the reaction vessel is isolated from excess sodium borohydride by hydrolysis with an aqueous solution of hydrochloric acid (200 milliliters HCl per two liters of distilled water). Upon precipitation of the isolated product, it is filtered, washed with alternate solutions of aqueous hydrochloric acid and distilled water, dried and recrystallized from benzene. The recovered product, 1-(2-anthryl) ethanol, is white in color. Yield: 50 grams, M.P. 164° C.

About 50 grams of 1-(2-anthryl) ethanol is dissolved in 375 milliliters of dioxane. To this solution is subsequently added 37.5 milliliters of triethylamine and 27.5 milliliters methacryloyl chloride. The condensation of the 1-(2-anthryl) ethanol and methacryloyl chloride is allowed to proceed for about 24 hours. After that time, the reaction between the 1-(2-anthryl) ethanol and methacryloyl chloride is quenched by the addition of water to the rection medium. Sufficient water is added to extract unreacted methacryloyl chloride from the reaction mass. The precipitate which forms is separated from the reaction medium by filtration, dried in a vacuum oven and recrystallized from a mixed solvent of benzene and methanol.

About 25 grams of monomer and about 0.05 grams azobisisobutyronitrile (5 milliliters of a solution of 0.5 grams azobisisobutyronitrile in 50 milliliters benzene) are charged to a light tight resin kettle containing 300 milliliters dried benzene. The reaction vessel is purged with nitrogen and its contents heated under mild agitation to 60° C and maintained at that temperature for 24 hours. The polymer is isolated from the reaction mass by precipitation with methanol and precipitated solids separated by filtration, washed with methanol and dried. The recovered solids are further purified by reprecipitation in acetone for removal of low molecular weight polymer fractions and unpolymerized monomer residues. Yield 26 grams, $\overline{M}_w$ 280,000 - as determined by standard light scattering techniques (Brice Pheonix Light Scattering Photometer).

The polymer thus prepared can now be dissolved in tetrahydrofuran and the resulting solution spray coated on a suitable conductive substrate. In order to remedy any irregularities in surface texture of such film, the coated substrate is placed on a hot plate and gradually heated in a non-oxidizing environment until it (the coating) begins to flow and thus any surface irregularities eliminated. The dry film thickness of the anthracene functional polymer coating thus prepared is in a range of about 15 microns. The resulting plate is evaluated in a standard Xerox Model D copier. Initial copies prepared from this plate have good solid density development and good resolution.

EXAMPLE XVI

A film of the polymer of Example XV is spray coated on a smooth Teflon Substrate. The coated Teflon substrate is heated sufficiently in a non-oxidizing environment to cause the polymer to flow together and thus eliminate any irregularities in the surface of the polymer coating. Sufficient polymer is sprayed onto the Teflon substrate to provide a polymer film thickness of approximately 50 microns. Subsequent to cooling of the polymer film the substrate bearing said film is placed in an evaporator and a photoconductive layer of amorphous selenium deposited on the surface of the polymer film. Sufficient selenium is deposited to form a photogenerator layer having a thickness of approximately 1 micron. The coated substrate is transferred to a second evaporator and a layer of aluminum 15 microns thick vacuum deposited on the surface of the selenium layer. The coated substrate is removed from the evaporator and the polymer/selenium/aluminum composite stripped from the Teflon surface of the substrate. This composite is then laminated to a conductive metal platen). (aluminum layer contiguous with the surface of said platen). The electrophotographic properties of the composite are now evaluated on a Xerox Model D copier. Such evaluation comprises initially charging the polymer surface of the composite in the dark to a positive potential of about 600 volts, followed by projection of image information on said surface. The source of illumination of the image information is white light. The resulting latent electrostatic image thus produced is developed by cascading a mixture of toner and carrier over the surface of the composite bearing the latent electrostatic image. The developed image is transferred to a sheet of paper and permanently affixed thereto by thermal fusion. Toner residues are removed from the image bearing surface of the composite and the copy cycle repeated. Copy quality is good and is reproducible.

EXAMPLE XVII

A composite similar to that of Example XVI is prepared by the substitution of a vacuum deposited layer of X-metal free phthalocyanine for selenium. Copy quality is good and is reproducible.

EXAMPLE XVIII

About 45 grams of polymer (prepared as described in Example XV) and 5 grams X-metal free phthalocyanine are dispersed in a common solvent and the resulting solution spray coated on a tin oxide coated glass plate (NESA glass). The polymer coating is heated on the plate until molten thus eliminating any surface irregularities in said coating. Sufficient polymer/phthalocyanine is deposited on the plate to form a substantially uniform binder layer having a dry film thickness of approximately 50 microns. The electrophotographic properties of this plate are evaluated in a Xerox Model D copier in the manner described in Example XVI. Such copies are of good quality and such quality is reproducible.

EXAMPLE XIX

About 30 moles of monomer prepared as described in Example XV are copolymerized with 70 moles methylmethacrylate. The random copolymer thus produced has substantially the same relative content of monomers as are present in the original charge. Upon separation and purification of the resulting copolymer it can be dissolved in tetrahydrofuran and dip or draw coated on an appropriate conductive substrate. Sufficient copolymer is transferred to the substrate to form a dry film having a thickness of about 40 microns. The electrophotographic properties of the imaging member thus prepared is evaluated in a Xerox Model D copier. Initial copy quality is good and such quality is reproducible.

EXAMPLE XX

The procedures of Example XIX are repeated except for the substitution of lauryl methacrylate monomer for the methylmethacrylate monomer used in preparation of the copolymer. Evaluation of the films prepared from this copolymer reveals performance equivalent to that of Example V.

EXAMPLE XXI - XXVI

The monomer synthesis of Example XV is repeated except for the substitution of the following acylating agents for acetic anhydride.

| Example No. | Acylating Agent |
|---|---|
| XXI | formyl chloride |
| XXII | acetyl chloride |
| XXIII | propionyl chloride |
| XXIV | butyryl chloride |
| XXV | valeryl chloride |
| XXVI | caproyl chloride |

What is claimed is:

1. In a process for preparation of a 2-anthryl or substituted 2-anthryl functional monomer wherein an anthracenic reactant of the formula

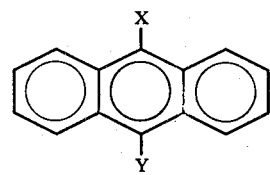

wherein
X and Y are independently selected from hydrogen, chlorine, bromine, alkyl of 1 to 4 carbon atoms or phenyl
is acylated at the 2-position, and thereafter modified by one or more additional steps at the carbonyl function to form the intended monomeric product, the improvement comprising:
(a) preparing a dispersion containing one or more of the above anthracenic reactants in an organic solvent comprising predominantly nitrobenzene; and
(b) contacting a solution containing a preformed acylating agent/Lewis Acid complex with the anthracenic reactant, the relative mole ratio of acylating agent to Lewis Acid in said solution being in the range of from about 0.5:1 to about 5:1 and the relative mole ratio of acylating agent to anthracenic reactant being in the range of from about 1:1 to about 5:1.

2. The process of claim 1 wherein the solution containing the preformed acylating/Lewis Acid complex is contacted with the anthracenic reactant by gradual addition of the complex to the anthracenic dispersion over a period of from about 15 minutes to about 60 minutes.

3. The process of claim 1, wherein the temperature of the solution resulting from contacting the dispersion of (a) with the complex of (b) is maintained within a range of from about 5 to about 50° C.

4. The process of claim 1, wherein the temperature of the solution resulting from contacting the dispersion of (a) with the complex of (b) is maintained within a range of from about 10 to about 30° C.

5. The process of claim 1, wherein the anthracenic reactant and the acylating agent/Lewis Acid complex, are allowed to react for an additional period of from about 1 to about 10 hours.

6. The process of claim 1, wherein the acylating agent/Lewis Acid complex is dissolved in a solvent comprising predominantly nitrobenzene.

7. The process of claim 1, wherein the relative weight ratio of anthracenic reactant to solvent is in the range of from about 1:4 to about 1:10.

8. The process of claim 1, wherein the anthracenic reactant is unsubstituted anthracene.

9. The process of claim 1, wherein the anthracenic reactant is substituted at the 9 and 10 position.

10. The process of claim 1, wherein the acylating agent is acetic anhydride.

11. The process of claim 1, wherein the Lewis Acid is aluminum chloride.

12. The process of claim 1, wherein the acylation of the anthracenic reactant is carried out in an inert non-oxidizing atmosphere.

13. The process of claim 1, wherein the solvent used in the dispersal of the anthracenic reaction consists essentially of nitrobenzene.

14. The process of claim 1, wherein the solvent used in preparation of the solution containing the preformed acylating agent/Lewis Acid complex consists essentially of nitrobenzene.

15. In a process for preparation of 2-anthryl or substituted 2-anthryl functional vinyl monomers wherein an anthracenic reactant of the formula

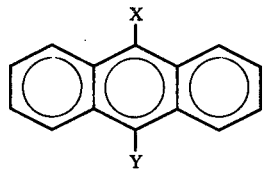

wherein
X and Y are independently selected from hydrogen, chlorine, bromine, alkyl of 1 to 4 carbon atoms or phenyl
is acylated at the 2-position, reduced to the corresponding alcohol and thereafter dehydrated thus forming the vinyl monomer, the improvement comprising:
(a) preparing a dispersion containing one or more of the above anthracenic reactants in an organic solvent comprising predominantly nitrobenzene; and
(b) contacting a solution containing a preformed acylating agent/Lewis Acid complex with the anthracenic reactant, the relative mole ratio of acylating agent to Lewis Acid in said solution being in the range of from about 0.5:1 to about 5:1 and the relative mole ratio of acylating agent to anthracenic reactant being in the range of from about 1:1 to about 5:1.

16. The process of claim 15, wherein the solution containing the preformed acylating/Lewis Acid complex is contacted with the anthracenic reactant by gradual addition of the complex to the anthracenic dispersion over a period of from about 15 minutes to about 60 minutes.

17. The process of claim 15, wherein the temperature of the solution resulting from contacting the dispersion of (a) with the complex of (b) is maintained within a range of from about 5° to about 50° C.

18. The process of claim 15, wherein the temperature of the solution resulting from contacting the dispersion of (a) with the complex of (b) is maintained within a range of from about 10° to about 30° C.

19. The process of claim 15, wherein the anthracenic reactant and the acrylating agent/Lewis Acid complex, are allowed to react for an additional period of from about 1 to about 10 hours.

20. The process of claim 15, wherein the acylating agent/Lewis Acid complex is dissolved in a solvent comprising predominantly nitrobenzene.

21. The process of claim 15, wherein the relative weight ratio of anthracenic reactant to solvent is in the range of from about 1:4 to about 1:10.

22. The process of claim 15, wherein the anthracenic reactant is unsubstituted anthracene.

23. The process of claim 15, wherein the anthracenic reactant is substituted at the 9 and 10 position.

24. The process of claim 15, wherein the acylating agent is acetic anhydride.

25. The process of claim 15, wherein the Lewis Acid is aluminum chloride.

26. The process of claim 15, wherein the acylation of the anthracenic reactant is carried out in an inert non-oxidizing atmosphere.

27. The process of claim 15, wherein the solvent used in the dispersal of the anthracenic reaction consists essentially of nitrobenzene.

28. The process of claim 15, wherein the solvent used in preparation of the solution containing the preformed acylating agent/Lewis Acid complex consists essentially of nitrobenzene.

29. A process for preparation of 2-anthryl or substituted 2-anthryl functional vinyl monomers wherein an anthracenic reactant of the formula

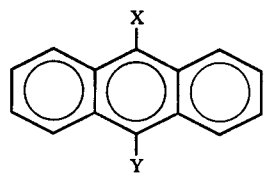

wherein
X and Y are independently selected from hydrogen, chlorine, bromine, alkyl of 1 to 4 carbon atoms or phenyl
is acylated at the 2-position, and directly converted to the corresponding vinyl monomer via a Wittig reaction, the improvement comprising:

(a) preparing a dispersion containing one or more of the above anthracenic reactants in an organic solvent comprising predominantly nitrobenzene; and (b) contacting a solution containing a preformed acylating agent/Lewis Acid complex with the anthracenic reactant, the relative mole ratio of acylating agent to Lewis Acid in said solution being in the range of from about 0.5:1 to about 5:1 and the relative mole ratio of acylating agent to anthracenic reactant being in the range of from about 1:1 to about 5:1.

30. The process of claim 29, wherein the solution containing the preformed acylating/Lewis Acid complex is contacted with the anthracenic reactant by gradual addition of the complex to the antracenic dispersion over a period of from about 15 minutes to about 60 minutes.

31. The process of claim 29, wherein the temperature of the solution resulting from contacting the dispersion of (a) with the complex of (b) is maintained within a range of from about 5° to about 50° C.

32. The process of claim 29, wherein the temperature of the solution resulting from contacting the dispersion of (a) with the complex of (b) is maintained within a range of from about 10° to about 30° C.

33. The process of claim 29, wherein the anthracenic reactant and the acylating agent/Lewis Acid complex, are allowed to react for an additional period of from about 1 to about 10 hours.

34. The process of claim 29, wherein the acylating agent/Lewis Acid complex is dissolved in a solvent comprising predominantly nitrobenzene.

35. The process of claim 29, wherein the relative weight ratio of anthracenic reactant to solvent is in the range of from about 1:4 to about 1:10.

36. The process of claim 29, wherein the anthracenic reactant is unsubstituted anthracene.

37. The process of claim 29, wherein the anthracenic reactant is substituted at the 9 and 10 position.

38. The process of claim 29, wherein the acylating agent is acetic anhydride.

39. The process of claim 29, wherein the Lewis Acid is aluminum chloride.

40. The process of claim 29, wherein the acylation of the anthracenic reactant is carried out in an inert non-oxidizing atmosphere.

41. The process of claim 29, wherein the solvent used in the dispersal of the anthracenic reaction consists essentially of nitrobenzene.

42. The process of claim 29, wherein the solvent used in preparation of the solution containing the preformed acylating agent/Lewis Acid complex consists essentially of nitrobenzene.

43. In a process for preparation of a 2-anthryl or substituted 2-anthryl functional vinyl monomer wherein an anthracenic reactant of the formula

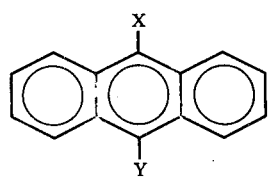

wherein

X and Y are independently selected from hydrogen, chlorine, bromine, alkyl of 1 to 4 carbon atoms or phenyl is acylated at the 2-position, reduced to the corresponding alcohol, the hydroxyl group of the alcohol displaced by a halogen atom and the resulting halide converted to the corresponding monomer by dehydrohalogenation, wherein the improvement comprises:

(a) preparing a dispersion containing one or more of the above anthracenic reactants in an organic solvent comprising predominantly nitrobenzene; and (b) contacting a solution containing a preformed acylating agent/Lewis Acid complex with the anthracenic reactant, the relative mole ratio of acylating agent to Lewis Acid in said solution being in the range of from about 0.5:1 to about 5:1 and the relative mole ratio of acylating agent to anthracenic reactant being in the range of from about 1:1 to about 5:1.

44. The process of claim 43, wherein the solution containing the preformed acylating/Lewis Acid complex is contacted with the anthracenic reactant by gradual addition of the complex to the anthracenic dispersion over a period of from about 15 minutes to about 60 minutes.

45. The process of claim 43, wherein the temperature of the solution resulting from contacting the dispersion of (a) with the complex of (b) is maintained within a range of from about 5° to about 50° C.

46. The process of claim 43, wherein the temperature of the solution resulting from contacting the dispersion of (a) with the complex of (b) is maintained within a range of from about 10° to about 30° C.

47. The process of claim 43, wherein the anthracenic reactant and the acylating agent/Lewis Acid complex, are allowed to react for an additional period of from about 1 to about 10 hours.

48. The process of claim 43, wherein the acylating agent/Lewis Acid complex is dissolved in a solvent comprising predominantly nitrobenzene.

49. The process of claim 43, wherein the relative weight weight ratio of anthracenic reactant to solvent is in the range of from about 1:4 to about 1:10.

50. The process of claim 43, wherein the anthracenic reactant is unsubstituted anthracene.

51. The process of claim 43, wherein the anthracenic reactant is substituted at the 9 and 10 position.

52. The process of claim 43, wherein the acylating agent is acetic anhydride.

53. The process of claim 43 wherein the Lewis Acid is aluminum chloride.

54. The process of claim 43, wherin the acylation of the anthracenic reactant is carried out in an inert non-oxidizing atmosphere.

55. The process of claim 43, wherein the solvent used in the dispersal of the anthracenic reaction consists essentially of nitrobenzene.

56. The process of claim 43, wherein the solvent used in preparation of the solution containing the preformed acylating agent/Lewis Acid complex consists essentially of nitrobenzene.

57. In a process for preparation of a 2-anthryl or substituted 2-anthryl acrylate monomer wherein an anthracenic reactant of the formula

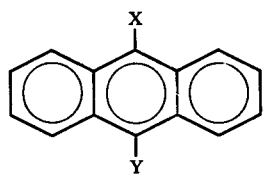

wherein

X and Y are independently selected from hydrogen, chlorine, bromine, alkyl of 1 to 4 carbon atoms or phenyl is acylated at the 2-position, reduced to the corresponding alcohol, and condensed with an acrylic acid or acrylic acid halide, the improvement comprising:

(a) preparing a dispersion containing one or more of the above anthracenic reactants in an organic solvent comprising predominantly nitrobenzene; and (b) contacting a solution containing a preformed acylating agent/Lewis Acid complex with the anthracenic reactant, the relative mole ratio of acylating agent to Lewis Acid in said solution being in the range of from about 0.5:1 to about 5:1 and the relative mole ratio of acylating agent to anthracenic reactant being in the range of from about 1:1 to about 5:1; and (c) condensing the acylated anthracenic reactant with an alpha alkyl acryloyl halide in a basic reaction medium, the relative mole ratio of alpha alkyl acryloyl halide to acylated anthracenic reactant being at least about 1:1.

58. The process of claim 57, wherein the solution containing the preformed acylating/Lewis Acid complex is contacted with the anthracenic reactant by gradual addition of the complex to the anthracenic dispersion over a period of from about 15 minutes to about 60 minutes.

59. The process of claim 57, wherein the temperature of the solution resulting from contacting the dispersion of (a) with the complex of (b) is maintained within a range of from about 5° to about 50° C.

60. The process of claim 57, wherein the temperature of the solution resulting from contacting the dispersion of (a) with the complex of (b) is maintained within a range of from about 10° to about 30° C.

61. The process of claim 57, wherein the anthracenic reactant and the acylating agent/Lewis Acid complex, are allowed to react for an additional period of from about 1 to about 20 hours.

62. The process of claim 57, wherein the acylating agent/Lewis Acid complex is dissolved in a solvent comprising predominantly nitrobenzene.

63. The process of claim 57, wherein the relative weight ratio of anthracenic reactant to solvent is in the range of from about 1:4 to about 1:10.

64. The process of claim 57, wherein the anthracenic reactant is unsubstituted anthracene.

65. The process of claim 57, wherein the anthracenic reactant is substituted at the 9 and 10 position.

66. The process of claim 57, wherein the acylating agent is acetic anhydride.

67. The process of claim 57, wherein the Lewis Acid is aluminum chloride.

68. The process of claim 57, wherein the acylation of the anthracenic reactant is carried out in an inert non-oxidizing atmosphere.

69. The process of claim 57, wherein the solvent used in the dispersal of the anthracenic reaction consists essentially of nitrobenzene.

70. The process of claim 57, wherein the solvent used in preparation of the solution containing the preformed acylating agent/Lewis Acid complex consists essentially of nitrobenzene.

* * * * *